(12) United States Patent
Givskov et al.

(10) Patent No.: US 9,655,840 B2
(45) Date of Patent: May 23, 2017

(54) WOUND CARE PRODUCTS

(75) Inventors: Michael Christian Givskov, Humlebaek (DK); Thomas Bjarnsholt, Søborg (DK); Klaus Kirketerp-Møller, Køge (DK)

(73) Assignees: RIGSHOSPITALET, COPENHAGEN UNIVERSITY HOSPITAL, Copenhagen Ø (DK); BISPEBJERG HOSPITAL, Copenhagen NV (DK)

( * ) Notice: Subject to any disclaimer, the term of this patent is extended or adjusted under 35 U.S.C. 154(b) by 248 days.

(21) Appl. No.: 13/517,406

(22) PCT Filed: Dec. 21, 2010

(86) PCT No.: PCT/DK2010/050352
§ 371 (c)(1),
(2), (4) Date: Nov. 14, 2012

(87) PCT Pub. No.: WO2011/076216
PCT Pub. Date: Jun. 30, 2011

(65) Prior Publication Data
US 2013/0060208 A1    Mar. 7, 2013

(30) Foreign Application Priority Data
Dec. 22, 2009  (DK) ................... 2009 70294

(51) Int. Cl.
*A61K 9/00* (2006.01)
*A61L 15/46* (2006.01)
(Continued)

(52) U.S. Cl.
CPC ............ *A61K 9/0014* (2013.01); *A61L 15/46* (2013.01); *A61L 26/0066* (2013.01);
(Continued)

(58) Field of Classification Search
CPC ............. A61M 1/0088; A61M 1/0023; A61M 1/0031; A61M 27/00; A61F 13/00068;
(Continued)

(56) References Cited

U.S. PATENT DOCUMENTS 4,366,170 A   12/1982  Engelhart et al.
5,480,658 A *  1/1996  Melman .................. A61K 8/19
                                                   252/182.12
(Continued)

FOREIGN PATENT DOCUMENTS

WO   WO 2005/058381 A1   6/2005
WO   WO 2005/123057 A1  12/2005
(Continued)

OTHER PUBLICATIONS

Akiyama et al. (Effects of acetic acid on biofilms formed by *Staphylococcus aureus*, Arch Dermatol Res; 1999; 291 :570-573).*
(Continued)

*Primary Examiner* — Philip R Wiest
*Assistant Examiner* — Ariana Zimbouski
(74) *Attorney, Agent, or Firm* — Knobbe Martens Olson & Bear, LLP (57) ABSTRACT

The present invention relates to wound care products, devices and methods incorporating acetic acid for the treatment of bacterial infections, in particular bacterial biofilm infections. In particular it relates to a wound care product comprising acetic acid, wherein the product comprises at least one further antibacterial compound; a delivery system comprising a container connected to a means of delivery which is connected to a pad, wherein said container comprises a composition comprising acetic acid and said pad comprises a self-adhesive material; a kit comprising a dressing and an adhesive membrane, wherein the dressing comprises a composition comprising acetic acid; a method of
(Continued)

Side view (objects not to scale)

treating a wound comprising a) applying acetic acid to the wound and b) applying a negative pressure to the wound.

8 Claims, 9 Drawing Sheets

(51) Int. Cl.
*A61L 26/00* (2006.01)
*A61M 1/00* (2006.01)
*A61M 27/00* (2006.01)
*A61F 13/00* (2006.01)

(52) U.S. Cl.
CPC ..... *A61L 26/0076* (2013.01); *A61F 13/00068* (2013.01); *A61L 2300/404* (2013.01); *A61L 2300/406* (2013.01); *A61M 1/0088* (2013.01); *A61M 27/00* (2013.01)

(58) Field of Classification Search
CPC ..... A61F 2013/00472; A61F 13/00063; A61K 9/0014; A61K 31/185; A61L 15/46; A61L 26/0066; A61L 26/0076
USPC .................... 604/290; 424/445, 447
See application file for complete search history.

(56) References Cited

U.S. PATENT DOCUMENTS

| | | | |
|---|---|---|---|
| 6,001,345 A | 12/1999 | Askill et al. | |
| 6,436,445 B1 | 8/2002 | Hei et al. | |
| 6,635,035 B1 | 10/2003 | Marasco et al. | |
| 2005/0250821 A1* | 11/2005 | Sewalt et al. | 514/358 |
| 2006/0025727 A1* | 2/2006 | Boehringer | A61M 1/0011 604/313 |
| 2007/0010798 A1* | 1/2007 | Stoller | A61M 1/0023 604/544 |
| 2007/0161625 A1* | 7/2007 | Brown | C09B 5/60 514/217.05 |
| 2007/0292397 A1* | 12/2007 | McNulty et al. | 424/93.6 |
| 2008/0125742 A1* | 5/2008 | Podhajsky | A61M 35/00 604/500 |
| 2009/0054855 A1* | 2/2009 | Blott | A61M 1/0058 604/290 |
| 2010/0030132 A1* | 2/2010 | Niezgoda | A61L 2/035 604/22 |
| 2010/0051035 A1* | 3/2010 | Jenkins et al. | 128/207.15 |
| 2010/0068279 A1 | 3/2010 | Hartwell | |
| 2011/0171283 A1* | 7/2011 | Riesinger | 424/445 |
| 2013/0196951 A1* | 8/2013 | Schoenfisch et al. | 514/63 |

FOREIGN PATENT DOCUMENTS

| | | |
|---|---|---|
| WO | WO 2008/013896 A2 | 1/2008 |
| WO | WO 2008/040020 A2 | 4/2008 |
| WO | WO 2008/129318 A2 | 4/2008 |
| WO | WO 2009/155931 A1 | 12/2009 |

OTHER PUBLICATIONS

Milner (Acetic acid to treat *Pseudomonas aeruginosa* in superficial wounds and burns, The Lancet; Jul. 4, 1992; 340, 8810: 61).*
Akiyama, Hisanori et al., "Effects of acetic acid on biofilms formed by *Staphylococcus aureus*" Arch Dermatol Res, 1999, pp. 570-573, vol. 291.
Hu, Li Donghong, "Biologic external application medicine for curing wound" PN—CN1724079 / PD—Jan. 25, 2006; XP-002583716.
Martineau, L. et al., "Biofilm reduction by a new burn gel that targets nociception" Journal of Applied Microbiology, 2007, pp. 297-304, vol. 103.
510K Summary; GelSpray Liquid Bandage 510k Summary; Submitter: BioCure, Inc. (5 pages).
Doyle, Ronald, "Microbial Growth in Biofilms: Special environments and physicochemical aspects," 2001, pp. 114-115, Gulf Professional Publishing.

* cited by examiner

Side view (objects not to scale)

Fig. 11 bottom view of pad

WOUND CARE PRODUCTS

CROSS REFERENCE TO RELATED APPLICATIONS

This application claims the benefit and priority to and is a U.S. National Phase Application of PCT International Application Number PCT/DK2010/050352, filed on Dec. 21, 2010, designating the United States of America and published in the English language, which is an International Application of and claims the benefit of priority to Danish Patent Application No. PA 2009 70294, filed on Dec. 22, 2009. The disclosures of the above-referenced applications are hereby expressly incorporated by reference in their entireties.

TECHNICAL FIELD OF THE INVENTION

The present invention relates to a wound care product and devices comprising acetic acid as an antimicrobial agent for the treatment of bacterial infections. The aspects of the invention include a wound care product, a delivery system, a kit, and a method.

BACKGROUND OF THE INVENTION

Microbes, in particular bacteria, are known to cause various types of infections in both humans and animals and also to cause problems in industrial equipment especially in cases were a high standard of hygiene is required. Antibiotics can be used to either kill or inhibit the growth of unwanted microbes and it is usually the choice of treatment for infections. However, the world wide increase in antibiotic resistant microbes has limited the effect of traditional treatments making it very difficult to treat infections that were once treatable. A particular problem is infections were the bacteria are capable of forming a so called biofilm as such infections typically tolerate the highest deliverable doses of antibiotics. Such infections develop commonly in wounds, which as a result, can develop into chronic wounds. Due to this antibiotic resistance and tolerance it is important to devise new treatment scenarios which efficiently enable eradication of unwanted microbes. Furthermore, in relation to infections in humans or animals it is imperative that the treatment is non-toxic to the hosts and physiologically acceptable.

Martineau L and Dosch H M (2007), Journal of Applied Microbiology, 103, 297-304 describes "Biofilm reduction by a new burn gel that targets nociception".

Akiyama H et al (1999); Arch Dermatol Res, 291, 570-573 describes "Effects of acetic acid on biofilms formed by *Staphylococcus aureus*".

International patent application number PCT/DK2009/050141 (presently unpublished) describes acetic acid compositions and there use in the treatment of bacterial biofilm infections.

In relation to wound care a number of products have been developed which have the combined effect of protecting the wound from the surrounding environment and enabling the delivery of compositions comprising active substances to the wound area. WO2005/058381 describes a wound care product comprising the active substance xylitol wherein the xylitol may be applied in a gel or a polymer onto a wound area for example by using gauze as support. WO2005/123057 describes a product for reducing and/or preventing bacterial infections of wounds comprising a composition including at least two weak organic acids and EDTA, along with bandage material.

Also reduced pressure devices where a reduced pressure is provided to a wound area have been developed. The methods used with these devices are called Negative Pressure Wound Therapy (NPWT). WO2008/013896 describes a sub-atmospheric pressure tissue treatment device wherein a cover defines a space between the tissue and the cover and a conduit is provided between this space and a means for providing sub-atmospheric pressure.

There is still, however, a need for effective products that include active substances which inhibit the growth of and/or kill bacteria, in particular there is a need for wound care products and methods that inhibit the growth of and/or kill biofilm forming bacteria more efficiently.

SUMMARY OF THE INVENTION

In their efforts to solve the abovementioned problems the present inventors have surprisingly found that applying acetic acid in certain ways to bacterial infections, in particular bacterial infections involving biofilm forming bacteria is highly effective towards clearing the infection and promote wound healing. In particular the inventors surprisingly found that acetic acid alone and in combination with other antibacterial agents, such as for example tobramycin, ciprofloxaxine, colistin and silver sulfadiazine, could be used alone or in novel devices that are applicable in wound healing methods. It was also found that the methods used comprising acetic acid and optionally other antibacterials were particularly effective when combined with Negative Pressure Wound Therapy (NPWT) methods.

Thus one aspect of the present invention is a wound care product comprising acetic acid, wherein the product comprises at least one further antibacterial compound.

Another aspect of the present invention is a delivery system comprising a container connected to a means of delivery which is connected to a pad, wherein said container comprises a composition comprising acetic acid and said pad comprises a self-adhesive material.

Another aspect of the present invention is a kit comprising a dressing and an adhesive membrane, wherein the dressing comprises a composition comprising acetic acid.

Yet another aspect of the present invention method of treating a wound comprising
 a) applying acetic acid to the wound
 b) applying a negative pressure to the wound

The present invention will now be described in more detail in the following.

DETAILED DESCRIPTION OF THE INVENTION

In the following the aspects of the present invention are described along with their preferred embodiments, the aspects being a delivery system, a kit, a method and a dressing comprising acetic acid. In the below text the term "wound" is to be understood in its broadest sense, i.e. as any exterior part of a human or animal body that may be in need of treatment, particularly antibacterial treatment. Examples of wounds in the present context includes but are not limited to: Any laceration to the skin, such as a wound, a chronic wound, a burn wound, a cut, wounds associated with dermatological conditions, grafts, pressure wounds, traumatic wounds, underlying infections with fistulation from bone, joint or soft tissue, any insertion or extrusion point for medical equipment, such as a catheter, or a medical bone screw, pins, wires, rods artificial joints, plates, autografts, allografts or zenografts.

Wound Care Product Comprising Acetic Acid

One aspect of the present invention is a wound care product comprising acetic acid, wherein the product comprises at least one further antibacterial compound.

In the present context "acetic acid" or a "composition comprising acetic acid" are interchangeable terms, and may include acetic acid as such, or liquid, solid or dry compositions thereof, including aqueous compositions. The compositions used may preferably comprise the features as described below. It may also be a dry or semi-dry composition of acetic acid which is dispersed in the wound care product, and activated upon wetting. A dry or semi-dry composition may for example be a powder wherein the acetic acid is absorbed prior to dispersion in the dressing.

Suitable concentrations of acetic acid in a composition include 0.01-20% wt/wt, such as 0.01-15% wt/wt acetic acid, or 0.01-10% wt/wt acetic acid, or 0.01-5% wt/wt acetic acid, or 0.05-20% wt/wt acetic acid, 0.05-15% wt/wt acetic acid, 0.05-10% wt/wt acetic acid, or 0.01-5% wt/wt acetic acid, 0.10-20% wt/wt acetic acid, 0.10-15% wt/wt acetic acid, 0.1-10% wt/wt acetic acid, or 0.10-5% wt/wt acetic acid, or 0.5-20% wt/wt acetic acid, or 0.5-15% wt/wt acetic acid, or 0.5-10% wt/wt acetic acid, or 0.5-5% wt/wt acetic acid, or 1.0-20% wt/wt acetic acid, or 1.0-15% wt/wt acetic acid, or 1.0-10% wt/wt acetic acid, or 1.0-5% wt/wt acetic acid, or 2.5-20% wt/wt acetic acid, or 2.5-15% wt/wt acetic acid, or 2.5-10% wt/wt acetic acid, or 2.5-5% wt/wt acetic acid, or 5-20% wt/wt acetic acid, or 5-15% wt/wt acetic acid, or 5-10% wt/wt acetic acid, or 10-20% wt/wt acetic acid, or 10-15% wt/wt acetic acid.

The inventors of the present invention have found that acetic acid in the non-dissociated form as given by the formula $CH_3COOH$ is capable of reducing microbial growth when it is present in its acidic form. In the context of the present invention the term "acidic form" used in relation to acetic acid means that it is present as $CH_3COOH$. As an equilibrium between $CH_3COO-$ and $CH_3COOH$ will exist when the pH is at the pKa value 4.76, 50% of the total amount of $CH_3COO-$ and $CH_3COOH$ is non-dissociated $CH_3COOH$ at the pKa value. As also shown in the examples, HCl does not exert a similar effect on microbial growth as acetic acid even when the two compounds are used at the same pH. This indicates that it is not the acidic pH which reduces the microbial growth but the acetic acid molecule itself in its non-dissociated form.

To maintain acetic acid in its active protonated form a buffer capable of maintaining acetic acid in its acidic form may be included in the composition comprising acetic acid. Preferably the buffer is a physiologically tolerable buffer capable of maintaining the acetic acid at a pH in the range of 2-7, such as in the range of 2-6.5, such as 2-6, or 2-5.5, or 2-5, or 2.5-7, or 2.5-6.5, or 2.5-6, or 2.5-5.5, or 2.5-5, or 3-7, or 3-6.5, or 3-6, or 3-5.5, or 3-5, or 3.5-7, or 3.5-6.5, or 3.5-6, or 3.5-5.5, or 3.5-5, or 4-7, or 4-6.5, or 4-6, or 4-5.5, or 4-5.

In the context of the present invention the term "physiologically tolerable buffer" is to be understood as buffers used according to the invention resulting in solutions that are nontoxic to recipients at the dosages and concentrations employed and which are sterile, endotoxin-free and pyrogen-free. Sterility and toxicity may be assessed according to the official monographs of U.S. Pharmacopeia e.g. sterility test USP 71, bacterial endotoxins test USP 85 and pyrogen test USP 151. Also a physiologically tolerable buffer in the present context is non-carcinogenic and non-mutagenic in the applied dosages and concentrations.

The term buffer is well known as a general description of a solution containing either a weak acid and its salt or a weak base and its salt, which is resistant to changes in pH. In the context of the present invention the term "buffer capable of maintaining acetic acid at a pH in the range of 2-7" is to be understood as a buffer which is capable of maintaining acetic acid in its acidic form also when the composition is added to e.g. a microbial biofilm in an infected wound. In this context the term "capable of maintaining" is to be understood as a buffer which is capable of maintaining the pH of the acetic acid in the specified interval for a period of more than 20 min, 30 min, 40 min, 50 min, 60 min, 70 min, 80 min, 90 min, 100 min, 110 min, preferably more than 2 hours, such as more than 3 hours, or more than 4 hours, or more than 5 hours, or more than 6 hours, or more than 7 hours, or more than 8 hours, or more than 9 hours, or more than 10 hours, or more than 15 hours, or more than 20 hours, or more than 24 hours, or more than 36 hours, or more than 48 hours, or more than 72 hours, or more than 96 hours, or more than 100 hours, or more than 150 hours.

Different buffers are capable of maintaining acetic acid at a pH in the range of 2-7 while being physiologically tolerable and examples of these include but are not limited to: sodium acetate, sodium bicarbonate, phosphate buffers, tris buffers and HEPES buffer. Thus in a preferred embodiment the composition comprising acetic acid contains a buffer selected from this group. One advantage of using a buffer in the composition comprising acetic acid is the capability of the buffer to maintain the pH at a given desired value for longer than the equivalent compositions with no buffer present. This is for example advantageous when applying the composition to patients since the acetic acid of the composition is active for longer periods of time and the composition need not be re-applied or changed as often as when no buffer is present. Importantly, toxic and/or carcinogenic buffers such as, triethanolamine, tri- and di-ethylamine and salts thereof are not comprised in the present invention as the composition is administered in relatively large amounts, possibly to compromised or sensitive tissue such as wounds.

Buffers are known to have different buffering capacities and the amount of buffer it is relevant to use therefore depends on among other things the concentration of acetic acid, the choice of buffer and the conditions under which the composition is to be used.

The composition comprising acetic acid is preferably sterile, i.e. it is essentially free of transmissible agents such as fungi, bacteria or viruses. A sterile composition may be achieved using sterile components and/or by sterilisation of the finished composition and/or by filtration through sterile filtration membranes, prior to being placed into a container having a sterile access port, for example, an intravenous solution bag or vial having a stopper pierceable by a hypodermic injection needle.

The inventors of the present invention have shown that when pH of the composition comprising acetic acid is 5 or above the presence of antibacterials such as for example tobramycin, ciprofloxaxine, colistin and silver sulfadiazine in the composition is able to exert a synergistic, antimicrobial effect with respect to decreasing the amount of viable bacteria compared to the same composition without an additional antibacterial agent. Hence it may be an advantage to include an antibacterial agent or antibiotic in the composition of the present invention especially if the pH of the composition is above 4.5, such as above 5

The antibacterial compound may preferably be an antibiotic, selected from the group consisting of amino glycosides, macrolides, fluoroquinolones, ceftazidimes, tetracyclines, sulfonamides, beta-lactams, oxazolidiones, antimicrobial peptides. In particular the antibiotic compounds tobramycin, ciprofloxaxine, and colistin has been proven effective in the treatment of infected wounds comprising biofilm forming bacteria when combined with acetic acid.

Alternatively the antibacterial compound is selected from the group consisting of xylitol, framycetin, fusidic acid, nitrofural, phenylmercuric nitrate, benzododecinium, triclosan, cetylpyridinium, aluminium chlorohydrate, povidone-iodine, clioquinol, benzalkonium, chlorhexidine, iodoform, hypochloric acid. In another embodiment the antibacterial compound is silver (Ag). The silver may either be in its ionic form $Ag^+$, e.g. as a silver salt or as silver metal e.g. nanosized silver particles. In particular silver sulfadiazine has been proven to have a synergistic effect in combination with acetic acid.

The wound care product may in another embodiment further comprise at least one growth factor, such as transforming growth factor, epidermal growth factor, platelet derived growth factor, insulin-like growth factor, keratinocyte growth factor, fibroblast growth factor, granulocyte macrophage colony stimulating growth factor, granulocyte colony stimulating growth factor.

The wound care product may also further comprise a compound selected from the group consisting of pH indicator, Ringer's solution and isotonic saline.

In another embodiment a wound care product is provided wherein said product is in the form of a spray, a gel, a dressing, a foam, or a paste.

In another embodiment a wound care product is provided which is a dressing, wherein said dressing comprises two or more layers. Said dressing may comprise two outer layers surrounding a core layer and wherein the core comprises an absorbant material.

The absorbant material of the dressing may preferably be selected from the group consisting of polyurethane-ether, polyacrylate, cellulose, polypropylene fibres, gauze, alginate, agar, or mixtures thereof. The outer layers of the dressing may comprise a material selected from non-woven polypropylene fibres, viscose or cotton (gauze).

Another aspect of the present invention is the wound care product as described above for use in treatment of bacterial infections in wounds, in particular bacterial infections comprising biofilm forming bacteria. The biofilm forming bacteria causing the infections described above may be gram-negative bacteria or gram-positive bacteria. The bacteria may be anaerobic or aerobic. Examples of such bacteria include but is not limited to *P. aeruginosa* and *S. aureus*.

In particular, the wound care product for use in treatment of bacterial infections in combination with Negative Pressure Wound Therapy has been shown to be effective, and the wound care product is adapted to such use, i.e. for example the dressing is made of a material well suited for use in Negative Pressure Wound therapy. The Negative Pressure Wound Therapy (NPWT) method is also known as Topical Negative Pressure (TNP) method, Sub-atmospheric Pressure Dressing (SPD) method, or Vacuum Sealing Technique (VST) method. These methods are known to the skilled person, and have among others the advantages of removing wound fluids and desiccated tissue, improving blood flow in the wound, and decreasing levels of bacteria in the wound. As described above, in the present context it may also help to remove excess or "spent" volumes of the wound care product comprising acetic acid.

Another aspect of the present invention is a method of treating a wound comprising
a) Applying a wound care product comprising acetic acid, wherein the product comprises at least one further antibacterial compound to a wound.

In particular the method described in combination with Negative Pressure Wound Therapy has been shown to be effective.

Delivery System Comprising Acetic Acid

Figure 11:
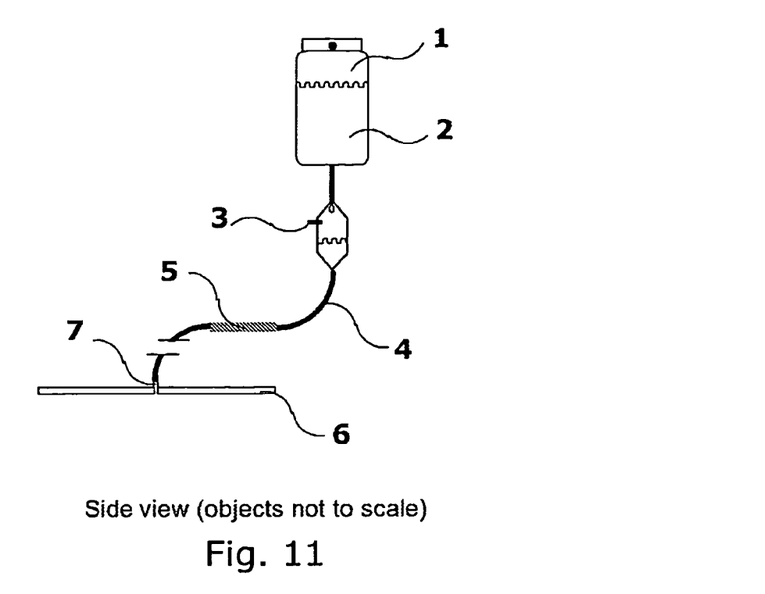
FIG. 11 shows a side view of a preferred embodiment of the delivery system of the present invention, which in this particular example comprises a container (1) connected to a means of delivery (4), such as a tube which is connected to a pad (6), wherein said container comprises a composition comprising acetic acid (2) and said pad (6) comprises a self-adhesive material (8). The orifice of the tube is connected to a tube connector or nozzle (7) penetrating the pad (6). The tube (4) has a section comprising a soft means of delivery such as a soft tube (5). A transparent drip chamber comprising an air nozzle (3) may be used to monitor and control composition delivery.
Figure 12:
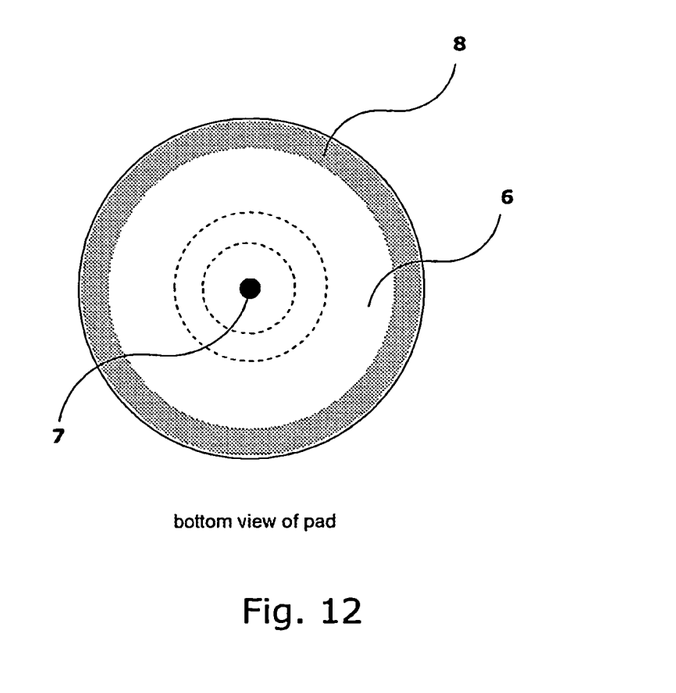
FIG. 12 shows a bottom view of the pad (6) comprised in the delivery system of the present invention, the pad (6) comprising a penetrating nozzle (7) and a self-adhesive material (8).

Another aspect of the present invention is a delivery system comprising a container (1) connected to a means of delivery (4) which is connected to a pad (6), wherein said container (1) comprises a composition comprising acetic acid (2) and said pad comprises a self-adhesive material (8) (see FIGS. 11 and 12).

In the context of the present invention the term "container" in the broadest sense is any container capable of holding a liquid. Herein, the container is capable of holding an acidic liquid, such as an acidic composition comprising acetic acid. The material of the container should also be chemically inert, i.e. it should not readily participate in any chemical reactions with the compositions of the present inventions or be a significant source of any chemical contaminants thereto. Examples of such containers include, but are not limited to: bags for fluids such as drip bags, or a vial having a stopper pierceable by a hypodermic injection needle. When in use the container may advantageously be positioned above the means for delivering the liquid hereby providing for gravity to act as a driving force for delivering the liquid. Pumps may however also be used as driving force with or without valves inserted in the pipeline to control flow and/or volume.

In a preferred embodiment the means for delivery may comprise a tube. Herein a "tube" is defined as a conduit, channel, tube or pipe capable of transporting liquids. The material of the tube should in particular be chemically inert, i.e. it should not readily participate in any chemical reactions with the compositions of the present inventions or be a significant source of any chemical contaminants thereto. Examples of such tubes include, but are not limited to: Medical tubing such as drip tubes. The tube may preferably be translucent to allow inspection of flow, air bubbles or blockage.

In the context of the present invention a "pad" is defined as a device which is flat or thin in the plane perpendicular to the surface to which it is attached, such as a dressing, and that may be either circular, rectangular, square or a custom shape in the plane that is aligned with the dressing or skin surface. The surface area of the aligned plane of the pad may vary, for example according to the size of a wound and/or the dressing. The pad includes means for connecting at least one conduit, such as a tube, and a self-adhesive material (see FIG. 12).

The advantages of using a pad, as compared to using just a tube, are that the relatively large surface area of the pad provides for better adherence to a given surface since a larger area can comprise a self-adhesive material. Also the pad shape enables the user to further fasten the pad to a surface such as a dressing in a wound by applying an adhesive membrane, such as an adhesive bandage, or gauze on top of the pad and around the tube connection point. The adhesive membrane or gauze may be custom made to fit around the pad comprising the tube fitting. Finally, the pad may be shaped in a way as to provide an enhanced distribution of fluid from the tube into a dressing, thereby better ensuring that the entire wound area is contacted with the composition comprising acetic acid.

A "self-adhesive material" as defined herein is a material which is capable of adhering to a surface. In particular it may be capable of adhering to a surface without any preliminary manipulations required to obtain the adhesive effect, such as heating, wetting or mixing components. In the context of this invention the self-adhesive material may typically already be adhering to the pad of the invention, and is readily capable of adhering to the dressing or the skin. The self-adhesive material may be protected by a film, such as a plastic film, which is removed prior to application to a dressing. Alternatively the adhesive material is comprised with the pad in a for example tube ready for application to the pad, prior to use. In the present context the adhesive material should be non-toxic, in particular it should be dermatologically non-toxic. Useful self-adhering materials include but are not limited to: silicone gel, addition curing Room Temperature Vulcanising (RTV) silicone systems, vapour permeable adhesive films, commercial products such as Dispomelt® 70-4647, Nusil-Med® 6340, Nusil-Med® 3-6300, Nusil-Med® 12-6300. In one embodiment of the present invention a delivery system is provided, wherein the self-adhesive material is placed on the side of the pad which is opposite to the side comprising the connection site or fitting for the tube.

The "composition comprising acetic acid" of the present delivery system is preferably a liquid composition comprising acetic acid ($CH_3COOH$). Preferably it is an aqueous composition of acetic acid. Useful embodiments of the composition are described in the above section regarding a wound care product.

Thus in one embodiment of the present invention the composition comprising acetic acid may further comprise an antibiotic. Examples of such suitable antibiotics include but are not limited to: amino glycosides, macrolides, fluoroquinolones, ceftazidimes, tetracyclines, sulfonamides, beta-lactams, oxazolidiones, and antimicrobial peptides. In particular tobramycin, ciprofloxaxine, and colistin has been shown to display synergistic effect in combination with acetic acid during treatment of infected wounds.

In another embodiment the composition comprising acetic acid may further comprise one or more antibacterial compounds selected from the group consisting of but not limited to: xylitol, framycetin, fusidic acid, nitrofural, phenylmercuric nitrate, benzododecinium, triclosan, cetylpyridinium, aluminium chlorohydrate, povidone-iodine, clioquinol, benzalkonium, chlorhexidine, iodoform. In another embodiment silver may be the antibacterial compound. In particular silver sulfadiazine has been shown to display synergistic effect in combination with acetic acid during treatment of infected wounds. Silver may be as described above in the section regarding a wound care product.

In yet another embodiment a growth factor is included in the composition, examples of growth factors are given above.

In another embodiment the composition comprising acetic acid may further comprise one or more compounds selected from the group consisting of but not limited to: detergents, disinfectants, ringer's solution, and isotonic saline.

In yet another embodiment of the present invention a drip chamber is incorporated in the tube of the present invention, preferably on a vertical section of the tube. By drip chamber is meant a chamber, preferably a translucent chamber, in the flow path of liquid composition transported in the tube wherein the liquid is dripping into a small liquid reservoir comprised in the drip chamber. In the bottom of said reservoir the liquid is allowed to continue onwards into the tube again. Such drip chambers are commercially available and known to the skilled person. The advantage of a drip chamber is the removal of air bubbles from the composition comprising acetic acid. Air bubbles can disrupt flow. Furthermore, it enables the user to monitor the flow of liquid.

Another embodiment is a delivery system further comprising an air nozzle (3) between the container and the pad. In the present context an air nozzle is defined as a means of allowing air to pass in an out of a volume defined by for example a container, chamber or a tube. The air nozzle may also comprise a means of hindering air flow through the nozzle, such as a lid or plug. The air nozzle may advantageously be situated on the drip chamber optionally comprised in the tube (see FIG. 11)

A preferred embodiment is a delivery system, wherein the tube is connected to the centre of the pad. As the pad is not necessarily symmetrical "the centre of the pad" is to be understood as the central part of the pad, i.e. a part of the pad that is not adjacent to an edge of the pad. This feature has the advantage that the user can apply adhesive material and/or gauze on top of the pad on all sides of the tube connector or nozzle (7), which then assists in holding the pad in the correct position for optimum distribution of fluid to e.g. a dressing, i.e. the pad is unable to slip out and/or to move around.

In another embodiment of the delivery system a tube is provided, which comprises a soft tube (5). The soft tube may be comprised as a section of the tube. The section may advantageously be of a length in the range of 2-100 cm, such as 5-50 cm, 7-40 cm, 8-30 cm, 9-20 cm, preferably 10-15 cm. A "soft tube" is a tube as defined above, which is adapted to be flexible or soft, i.e. it made from a flexible material. The soft tube is sufficiently soft to adapt to medical pumps, as for example pumps that function by compressing the tube in the direction of the flow (a peristaltic pump). Peristaltic pumps for medical use are well known to the skilled person. A soft tube also allows for the use of a mechanical clamp to act as a external valve. Internal valves may also be used, such as valves inserted serially in between sections of tubing. The tube is also sufficiently soft to allow adaption to inlet and outlet nozzles of any medical equipment used for the present invention such as for example non-peristaltic medical pumps or a syringe. Thus, the user will not have to adapt the tube of the present invention to medical equipment requiring a soft tube or a hard tube, as both tube materials are incorporated in this preferred embodiment.

In a particular useful embodiment of the delivery system, it is adapted for use in combination with NPWT methods. Such adaptations include but are not limited to the soft tube as described above, which will be adaptable with a means for providing a negative pressure such as a peristaltic pump. Also the pad may be adapted for effectively applying the negative pressure to a large area of for example a dressing, and it may also be adapted to fit two tubes, i.e. one for the delivery system and one for the means to apply a negative pressure.

Kit Comprising Acetic Acid

Another aspect of the present invention is a kit comprising a dressing (9) and an adhesive membrane (10), wherein the dressing comprises a composition comprising acetic acid.

A dressing as defined herein is a material that can be applied to a wound, said material being capable of absorbing and releasing a liquid. The dressing material may be nylon, polyester, acrylic, rayon, viscose, cotton (gauze), polyurethane, other polymeric materials, cellulose materials, a reticulate foam or mixtures thereof. In the present context "Reticulate foam" means foam comprising a cross-linked polymer material. Such materials may include but are not limited to: polyurethane-ether, polyacrylate, cellulose, polypropylene fibres, alginate, viscose, agar, or mixtures thereof.

Figure 13:
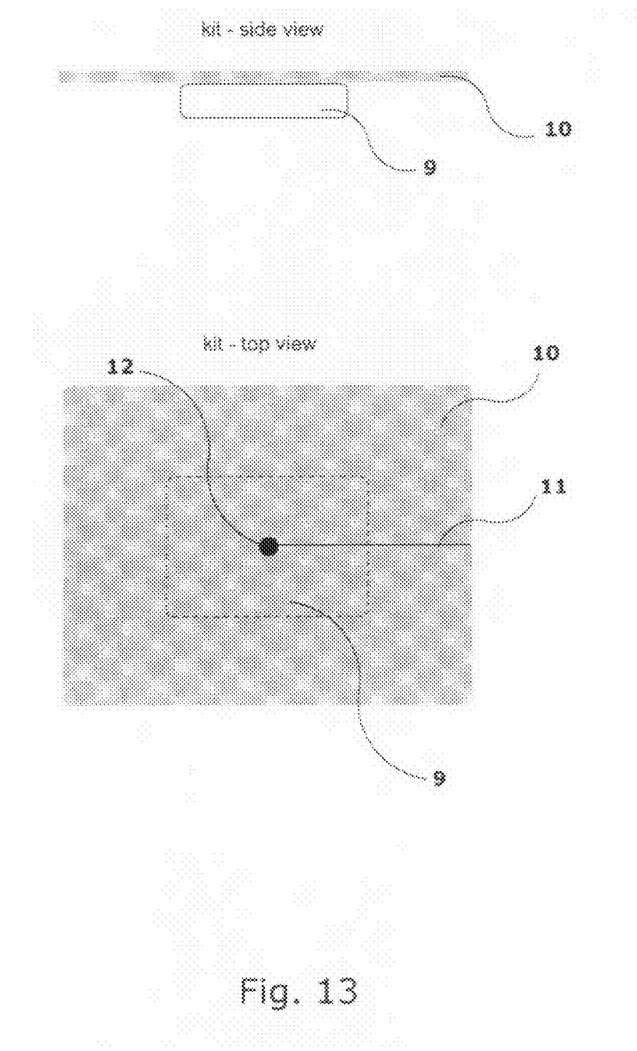
FIG. 13 shows a side and top view of the kit comprising a dressing (9) and adhesive membrane (10) of the present invention. The adhesive membrane comprising a cut-through (11) for insertion of one or more tubes, and a hole or cut-out (12) in the middle for placement of the one or more tubes. Said tube may be delivery tubes and/or drainage tubes.

An "adhesive membrane" as defined herein is any membrane capable of covering the dressing provided in the kit while being able to adhere to the surface area surrounding the wound and dressing. It may also adhere to the dressing itself. An example of this would be a self-adhesive plaster, bandage, or tape of sufficient size and shape. A membrane such as a plaster, bandage or tape may advantageously be adapted to allow e.g. tubing to pass through it, e.g. via a cut-through (11) and a central penetrating cut-out (12) (see FIG. 13). This allows for liquids to be delivered or removed from the dressing and wound area. However, within the meaning of adhesive membrane is also gauze, which does not necessarily comprise an adhesive material, but adheres to the area of the wound via the force, provided by wrapping the gauze around the body-part inflicted with a wound. This may be especially relevant for wounds affecting the limbs, i.e. arms, hands, legs and feet, where gauze may be easier to apply than a plaster or tape, and also may hold the dressing in the desired position better than a plaster or tape (see FIG. 13).

The composition comprising acetic acid comprised in the dressing of the kit may be as described in the section above regarding a wound care product.

In yet another embodiment a kit is provided, wherein said kit further comprises a drainage tube. A "drainage tube" as defined herein is a conduit, channel, tube or pipe as defined above capable of transporting liquids away from the dressing and thereby the wound area. The kit may also comprise a pad as described above, which is attachable to the drainage tube. The pad gives the abovementioned advantages of holding the tube in position and providing a larger area of attachment and suction (if suction is applied).

The kit may in a useful embodiment be adapted for use in combination with NPWT methods, e.g. the drainage tube may be adapted to fit into a NPWT device or pump. The drainage tube may for example be a soft tube as described above, which fits into a pump used for providing a negative pressure. Alternatively the dressing material is selected from materials allowing for a negative pressure to be evenly distributed throughout the wound area.

Method Comprising Acetic Acid

Another aspect of the present invention is a method of treating a wound comprising
  a) applying a composition comprising acetic acid to the wound
  b) applying a negative pressure to the wound The composition comprising acetic acid may be as defined in the previous section.

In the context of the present invention "negative pressure" is defined as a pressure within a given volume which is lower than the surrounding pressure, e.g. the ambient pressure which will often be atmospheric pressure. In the present context said volume may be the volume defined by an adhesive membrane, such as a bandage or gauze, placed over an area comprising a wound, preferably comprising a dressing in the wound cavity. The size of the wound, the adhesive membrane and the dressing determines the size of the volume. The volume may also be affected by the compressibility of the dressing. An effect of the negative pressure is to provide for the continuous removal of excess liquids such as exudates from a wound. In the present context it may also help to remove excess or "spent" volumes of the composition comprising acetic acid.

In one embodiment the composition comprising acetic acid is applied via a dressing. The dressing may comprise the composition or the composition may be added to the dressing in situ.

The composition comprising acetic acid may be applied for a period of 10-40 min, such as 15-35 min, preferably 20-30 min. The starting point of these periods is when the composition comprising acetic acid is put in contact with the wound, and the end point is defined as when the negative pressure is applied. The negative pressure may be applied for a period in the range of 0.5-18 h, such as 1-12 h, such as 2-8 h, such as 3-6 h, such as 4 h. Typically the period of applying negative pressure is interrupted by a new application of composition comprising acetic acid, whereafter said negative pressure is reapplied as described below. During any given interruption of the negative pressure the dressing may be changed.

In one embodiment a method is provided, wherein the negative pressure is applied by a Negative Pressure Wound Therapy (NPWT) method, also known as Topical Negative Pressure (TNP) method, Sub-atmospheric Pressure Dressing (SPD) method, or Vacuum Sealing Technique (VST) method. These methods are known to the skilled person, and have among others the advantages of removing wound fluids and desiccated tissue, improving blood flow in the wound, and decreasing levels of bacteria in the wound. As described above, in the present context it may also help to remove excess or "spent" volumes of the composition comprising acetic acid.

In yet another useful embodiment a method is provided, wherein steps a) and b) as described above are repeated, i.e. steps a) and b) are performed followed be performing steps a) and b) again, and so on. This repetitive cycle may be performed any number of times, and advantageously at least until any infection in the wound has been eradicated. The cycle may also be repeated until the wound has healed entirely thereby hindering any reinfection or so called super-infections.

The composition comprising acetic acid may be applied using the delivery system comprising a container, tube and pad comprising adhesive material as described for the above delivery system. The tube used in the delivery system may advantageously be disconnected from the container and connected to a medical pump to apply a negative pressure during step b). In another embodiment where the tube is already applied to a peristaltic pump to deliver the composition in step a), the tube may simply be disconnected from the container where after the pump direction is reversed to apply the negative pressure of step b), optionally combined with valves in the pipeline to control volume and/or flow and/or direction of flow.

The method may involve one tube as described for the delivery system of the present invention, i.e. a tube for delivering the composition comprising acetic acid, and an additional tube used for the NPWT device (e.g. the medical pump) by which the negative pressure is provided. The additional tube may in one embodiment be the drainage tube of a kit as described above. The two tubes may be inserted into one pad according to the present invention having been adapted to attachment of two tubes, or alternatively two separate pads may be used, optionally combined with valves in the pipeline to control volume and/or flow and/or direction of flow.

In another embodiment of this method the composition comprising acetic acid is applied using the kit comprising a dressing comprising acetic acid, and an adhesive membrane as described in the above section regarding a kit. Where the kit comprises a drainage tube this may advantageously be used in the application of the negative pressure during NPWT.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Material and Methods

Bacterial Strains

The wild-type *P. aeruginosa* PAO1 used for the planktonic and biofilm experiments was obtained from the

*Pseudomonas* Genetic Stock Center (www.pseudomonas-.med.ecu.edu, strain PAO0001). The wild-type *S. aureus* 8325-4, used for planktonic and biofilm experiments was described by Novick, R. P. 1967.

The clinical isolates of *P. aeruginosa* were obtained from chronically infected cystic fibrosis patients at the University Hospital of Copenhagen.

Growth Media

For plating, Luria broth (LB) medium mix with 2.0% agar was used. For all experiments including bacterial biofilms, AB minimal medium supplemented with glucose was used except if different is mentioned. AB minimal medium consists of: A standard buffer system consisting of $(NH_4)_2SO_4$ (15.1 mM), $Na_2HPO_4.2H_2O$ (33.7 mM) and $KH_2PO_4$ (22.0 mM. NaCl (0.051 M), $MgCl_2$ (1 mM), $CaCl_2$ (0.1 mM), and trace metals (100 µl/liter). The trace metal solution contained $CaSO_4.2H_2O$ (200 mg/liter), $FeSO_4.7H_2O$ (200 mg/liter), $MnSO_4.H_2O$ (20 mg/liter), $CuSO_4.5H_2O$ (20 mg/liter), $ZnSO_4.7H_2O$ (20 mg/liter), $CoSO_4.7H_2O$ (10 mg/liter), $NaMoO_4.H_2O$, and $H_3BO_3$ (5 mg/liter). Furthermore, experiments where the standard buffer system of the AB minimal medium was replaced by sodium acetate were performed in all the below examples. The exchange of buffer did not affect the results.

Growth of Bacteria

Two types of biofilm setups were used, a continuous flow system and a static system:

The continuous flow system is based on once through flow chambers perfused with sterile AB minimal medium containing 0.3 mM glucose as described by Christensen et al. (1999).

The static biofilm setup is based on biofilms growing in microtiter dishes with AB minimal medium containing 0.3 mM glucose as described by O' toole et al (1999). Planktonic cultures were grown in shake flasks at 37° C.

Antimicrobial Treatments

Continuous flow biofilm tolerance to acetic acid was assessed by growing *P. aeruginosa* or *S. aureus* biofilms for three days, then subsequently at day three to four supplementing the AB minimal medium with different concentrations of acetic acid or HCl (HCL served as a as control to acetic acid treatments).

Static biofilm tolerance to acetic acid was assessed by exchanging the AB minimal medium of 24 h old biofilms with AB minimal medium supplemented with different concentrations of acetic acid or HCl as control. To raise the pH of either acetic acid or HCl, NaOH was added in different concentrations.

Example 1

The efficacy of acetic acid with respect to eradication of mature biofilms was tested by treating a 3-day-old flow chamber biofilm of either *P. aeruginosa* or *S. aureus* with 0.5% and 1.0% acetic acid for 24 hours. Due to the buffer capacity of the AB minimal medium used, the pH of the solution became 4.33. As control similar biofilms were treated with AB minimal medium adjusted to pH 4.33 using HCl. After the treatment the biofilm biomasses were harvested mechanically from the flow chambers and plated on LB plates for determination of viability. Treatment with either 0.5 or 1.0% acetic acid completely eradicated *P. aeruginosa* biofilms, whereas the HCl treatment had no effect. As for *S. aureus* treatment with 0.5% acetic acid reduced the number of viable cells, whereas complete eradication was obtained using 1.0% acetic acid.

Example 2

To verify whether the killing capacity of the treatment in example 1 was due to acetic acid alone and not a combination of the constituents of the medium, the experiment in example 1 was repeated using 0.5% or 1.0% acetic in sterile miliQ water in contrast to AB minimal medium supplemented with glucose. Complete eradication was observed when harvesting 0.5% acetic acid treated *P. aeruginosa* and 1.0% acetic acid treated *S. aureus* biofilms, compared to the controls.

Example 3

The kinetics of antimicrobial activity against mature biofilms was tested by treating a 3-day-old continuous flow chamber biofilms of either *P. aeruginosa* with 0.5% or *S. aureus* with 1.0% acetic acid for 24 hours. Due to the buffer capacity of the AB minimal medium used the pH of the solution became 4.33. As control similar biofilms were treated with AB minimal medium adjusted to pH 4.33 by addition of HCl. After the treatment the biofilms were harvested mechanically, by scraping with a sterile scalpel, from the flow chambers and plated on LB plates for determination of viable counts. Complete killing of all bacteria was reached after 3 hours using 0.5% acetic acid against *P. aeruginosa* and 1.0% against *S. aureus*.

Example 4

Figure 1:
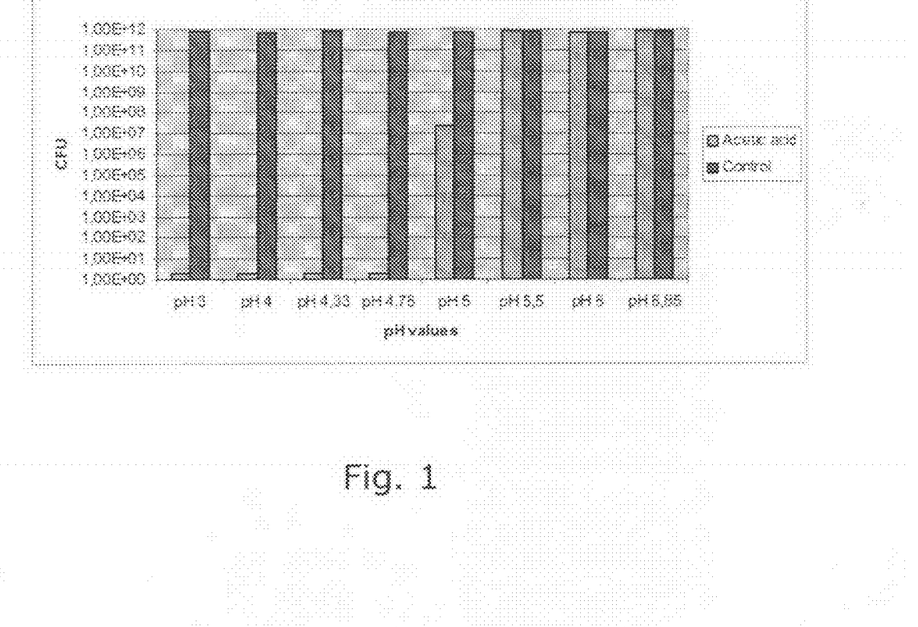
FIG. 1 shows antimicrobial effect of 0.5% acetic acid on 24 hours old static *P. aeruginosa* biofilms grown in AB minimal medium adjusted to different pH values. AB minimal medium without acetic acid adjusted to different pH values was used as control. The biofilm bacteria were harvested and plated on LB plates in order to determine the CFU after treatment (For visual appearance "no growth" is arbitrarily given a CFU value of 2).

To elucidate the pH dependency of the antimicrobial effect of acetic acid static 24 hour old biofilms were treated with a selection of 0.5% acetic acid solutions with increasing pH. Acetic acid in the AB minimal medium resulted in a pH value of 4.33, lower pH values were obtained by addition of HCl whereas higher pH values by addition of NaOH. This was compared to AB minimal media adjusted to the same range of pH by HCl or NaOH alone. As seen from FIG. 1, acetic acid eradicated biofilms of *P. aeruginosa* in the pH interval 3-4.76. At pH 5 a reduced effect is observed whereas at pH 5.5 and above no effect of acetic acid is observed. This pH dependency is due to the dissociation of acetic acid, which is at equilibrium at pH 4.76 (pKa value). Below pH 4.76 the equilibrium is shifted to the left i.e. acetic acid, and above pH 4.76 the equilibrium is shifted to the right i.e. the corresponding base.

$$CH_3COOH \Longrightarrow CH_3COO^- + H^{+pH>4.76}$$

$$CH_3COOH \Longleftarrow CH_3COO^- H^{+pH<4.76}$$

$$CH_3COOH = CH_3COO^- + H^{+pH=4.76}$$

The results of the present experimental scenario demonstrate that it is not an acidic effect (low pH values) per se which is the cause of the kill; it is the acetic acid molecule itself.

Example 5

Figure 2:
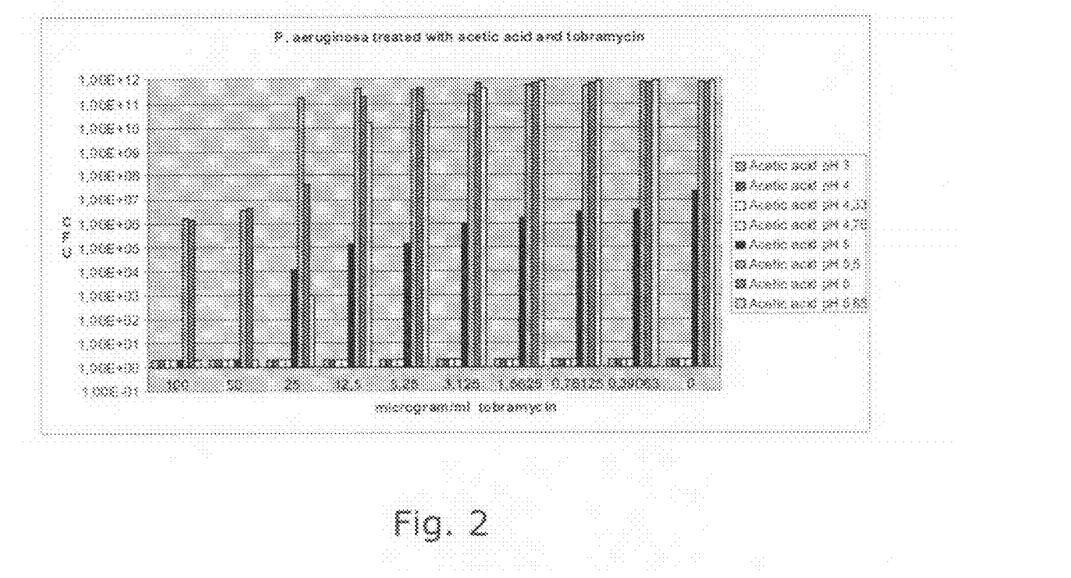
FIG. 2 demonstrates the antimicrobial effect of 0.5% acetic acid in synergy with increasing concentrations of tobramycin on 24 hour old static *P. aeruginosa* biofilms at pH 3 to 6.85. AB minimal medium supplemented with increasing concentrations of tobramycin served as control. The biofilm were harvested and plated on LB plates to determine the CFU after treatment (For visual appearance "no growth" is arbitrarily given a CFU value of 2).
Figure 3:
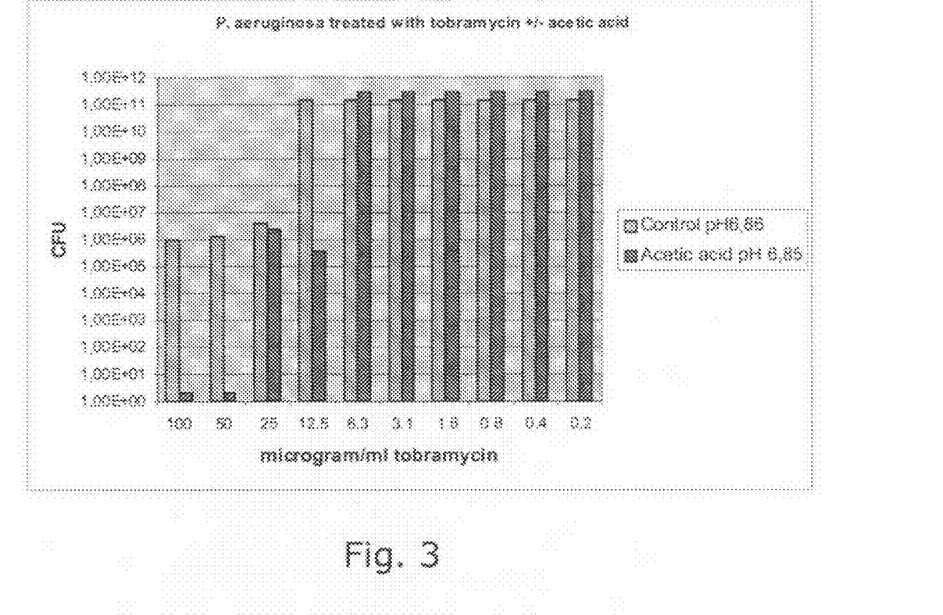
FIG. 3 demonstrates the synergistic antimicrobial effect of 0.5% acetic acid at different pH values with increasing concentrations of tobramycin on 24 hour old static *P. aeruginosa* biofilms. AB minimal medium without acetic acid, but supplemented with increasing concentrations of tobramycin served as control. The biofilm bacteria were harvested and plated on LB plates in order to determine the CFU after treatment (For visual appearance "no growth" is arbitrarily given a CFU value of 2).

To elucidate a synergistic antimicrobial effect of acetic acid and antibiotics, static biofilms of *P. aeruginosa* were grown for 24 hours prior to subsequent treatment with increasing concentrations of tobramycin and 0.5% acetic acid in the pH interval 3-6.85. The pH was adjusted by supplementing the AB minimal medium with either HCl or NaOH. When comparing acetic acid at pH 6.85 with and without tobramycin (FIG. 1, 2) a synergistic, antimicrobial effect exists between acetic acid and antibiotics. With pH values above 4.76, (FIG. 1) which is the dissociation point for acetic acid, the effect of acetic acid alone is decreasing. Acetic acid alone at pH 6.85 has no antibacterial effect on the bacteria (FIG. 1) however in the presence of tobramycin an effect on viable counts was observed including at pH 6.85 (FIG. 2). Tobramycin alone reduced the bacterial viability 5 fold at concentrations above 12.5 µg/ml (see FIG. 3). Acetic acid combined with tobramycin reduced the bacterial viability at pH values above 4.76 and showed a greater effect on viability than tobramycin alone (FIG. 3). In addition to tobramycin, the antibacterial substances ciprofoxaxine, colistin and silver sulfadiazine were also tested and display analogous synergistic effects.

Example 6

Figure 4:
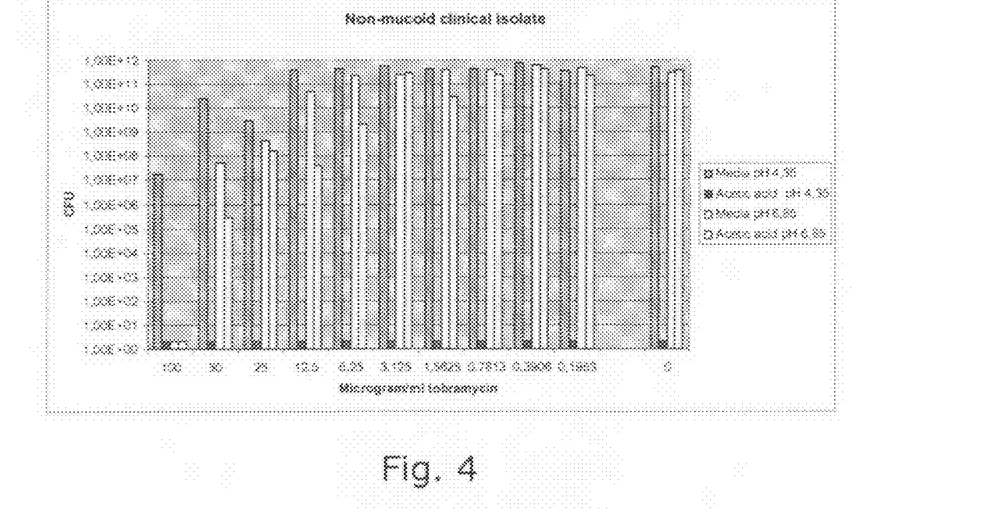
FIG. 4 demonstrates the synergistic, antimicrobial effect of 0.5% acetic acid at different pH values in combination with increasing concentrations of tobramycin on 24 hour old static biofilms on a clinical non-mucoid *P. aeruginosa* isolate. AB minimal media without acetic acid but supplemented with increasing concentrations of tobramycin served as control. The biofilm were harvested and plated on LB plates to determine the CFU after treatment (For visual appearance "no growth" is arbitrarily given a CFU value of 2).

To evaluate the clinical antimicrobial potential of acetic acid, static biofilms of clinical P. aeruginosa isolates were treated with acetic acid as described for example 5. As seen from FIG. 4, acetic acid eradicates the biofilms at a pH value below the dissociation point (pH 4.76) of acetic acid. Additionally the same synergistic effect between acetic acid and antibiotics is seen as for example 5.

Example 7

Figure 5:
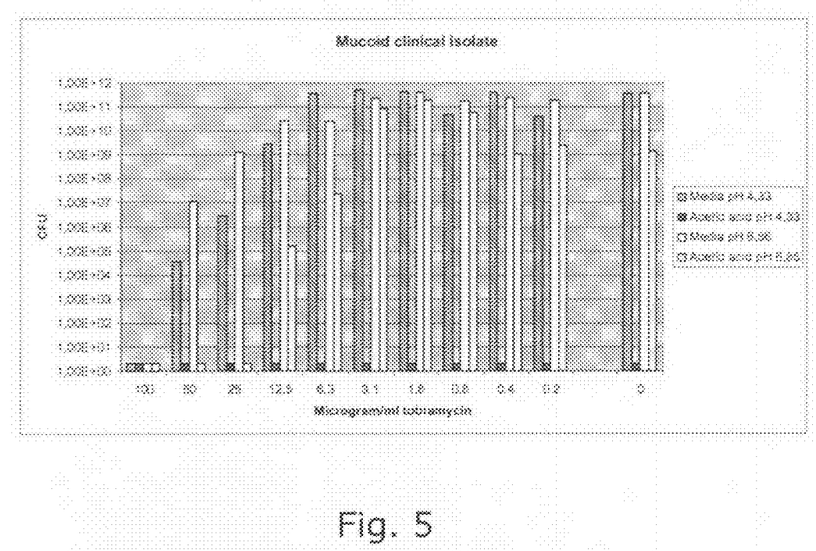
FIG. 5 demonstrates the synergistic, antimicrobial effect of 0.5% acetic acid at different pH values in with increasing concentrations of tobramycin on 24 hour old static biofilms of a clinical mucoid *P. aeruginosa* isolate. AB minimal medium without acetic acid, but supplemented with increasing concentrations of tobramycin was used as control. The biofilm were harvested and plated on LB plates to determine the CFU after treatment (For visual appearance "no growth" is arbitrarily given a CFU value of 2).

To evaluate the clinical potential of acetic acid towards the clinical important mucoid (alginate over-producing) P. aeruginosa phenotype, static biofilms of clinical isolated mucoid P. aeruginosa were treated with acetic acid as described for example 5. As seen from FIG. 5, acetic acid eradicates the biofilms at a pH value below the dissociation point (pH 4.76) of acetic acid. Additionally the same synergistic effect between acetic acid and antibiotics is seen as for example 5.

Example 8

Figure 6:
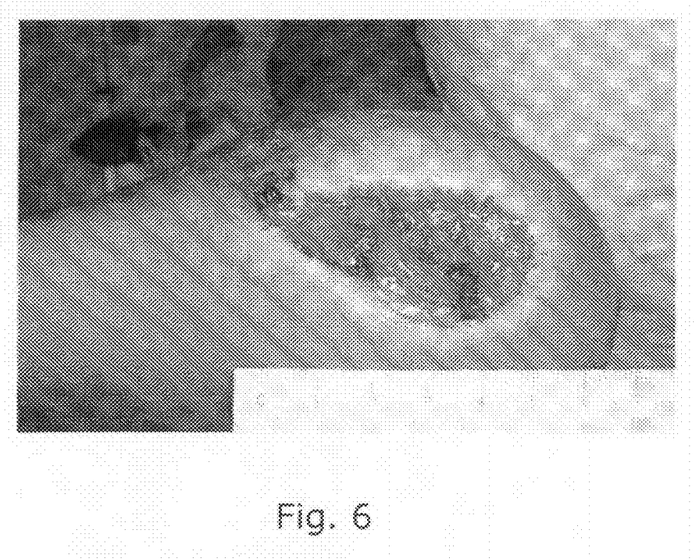
FIG. 6 shows a chronic heel ulcer infected with *P. aeruginosa* in a 38 year old male patient with type 2 mellitus diabetes prior to treatment with the wound care product of the present invention in combination with NPWT comprising buffered acetic acid solution (day 0). At this stage several well known antibacterial treatments had been tried.
Figure 7:
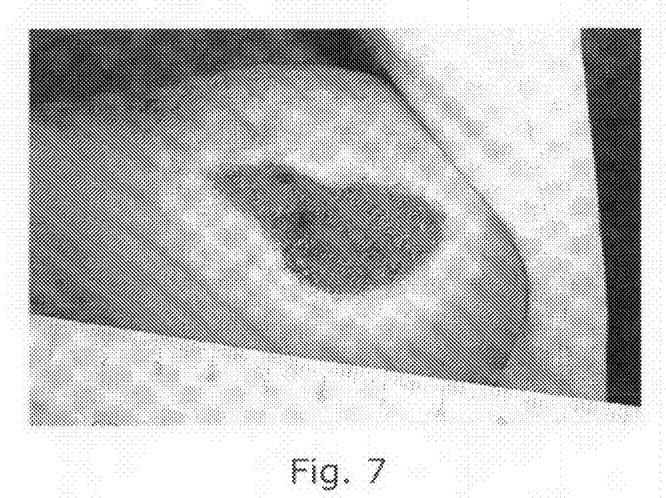
FIG. 7 shows the heel ulcer of FIG. 6 after 11 days of treatment with the wound care product of the present invention in combination with comprising buffered acetic acid solution (day 11). The mucoid infection has been eradicated and the ulcer is now healing normally.

To further evaluate the clinical potential of buffered 0.5% acetic acid solution towards the clinical important mucoid (alginate over-producing) P. aeruginosa phenotype, it was tested in the treatment of a chronic heel ulcer.
Medical History:
A 38 year old male with type 2 mellitus diabetes associated neuropathy was presented to a wound healing clinic. A heel ulcer was obtained during a vacation due to strenuous walking. The 38 year old male had the following prior history of treatment with no apparent improvement in wound healing (over period of three months):
  Off-loading, therapeutic shoes and aircast.
  Wound treatment with silver dressings and compression.
  Several courses of antibiotics.
Treatment:
  Treatment of the chronic wound (FIG. 6 [day 0]) with phosphate buffered 0.5% acetic acid (patient continued antibiotic therapy) was performed 6×20 minutes per day in combination with Negative Pressure Wound Therapy, for 11 days (continuous). On day 11 the infection had been eradicated and wound healing had begun as shown in FIG. 7 (day 11).

Example 9

Figure 8:
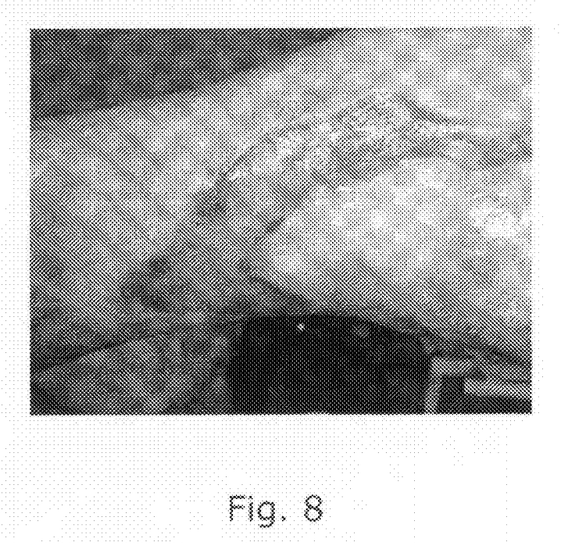
FIG. 8 shows a chronic leg ulcer infected with *P. aeruginosa* in a 73 years old female patient with type 2 mellitus diabetes prior to treatment with the wound care product of the present invention in combination with NPWT comprising buffered acetic acid solution (day 0). Cultures prior to treatment have shown *Pseudomonas aeruginosa* and *Staphylococcus aureus*. The patient received anti-*Staphylococcus* treatment due to infected toe on the contralateral leg (Heracillin).
Figure 9:
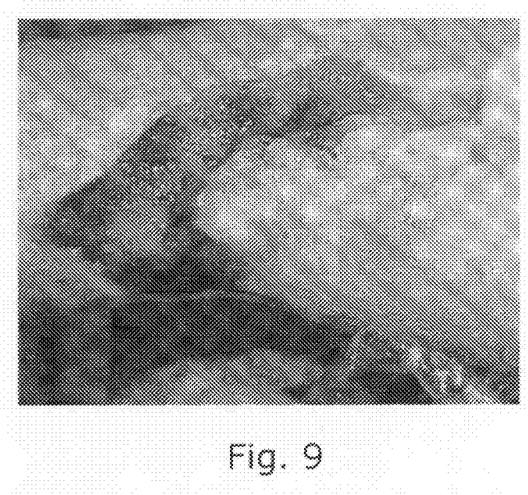
FIG. 9 shows the leg ulcer of FIG. 8 after 3 days of treatment with the wound care product of the present invention in combination with NPWT comprising buffered acetic acid solution (day 3). The mucoid infection has been significantly reduced and the ulcer has attained a dark red color indicating reestablishment of the normal wound healing process.
Figure 10:
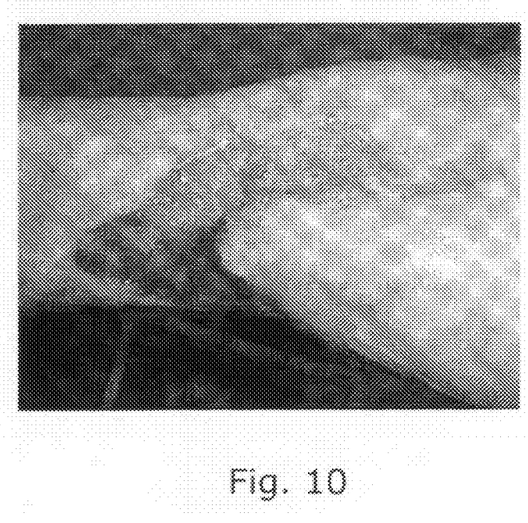
FIG. 10 shows the leg ulcer of FIGS. 8 and 9 after 6 days of treatment with the wound care product of the present invention in combination with NPWT comprising buffered acetic acid solution (day 6). The mucoid infection has been eradicated and the ulcer is now healing.

To further evaluate the clinical potential of buffered acetic acid solution towards the clinical important mucoid (alginate over-producing) P. aeruginosa phenotype, it was tested in the treatment of a chronic leg ulcer.
Medical History:
A 73 years old female with type 2 mellitus diabetes and a 3 year long history of leg ulcers. The patient have received an ulcer debridement and split skin transplant in 2006 with only temporarily success as the ulcer reoccurred after 3 months. The patient was considered unfit for a new operation de to her heart condition. Cultures prior to treatment have shown Pseudomonas aeruginosa and Staphylococcus aureus. The patient received anti-Staphylococcus treatment due to infected toe on the contralatteral leg (Heracillin).
Treatment:
  Treatment of wound (FIG. 8 [day 0]) with phosphate buffered acetic acid (patient continued antibiotic therapy) was performed 6×20 minutes per day, for 6 days (continuous) in combination with Negative Pressure Wound Therapy. After 3 days a significant improvement in the wound healing process was evident as shown in FIG. 9 (day 3) and after 6 days the infection was eradicated and the wound healing process was proceeding well as shown in FIG. 10 (day 6).

Example 10

Figure 14:
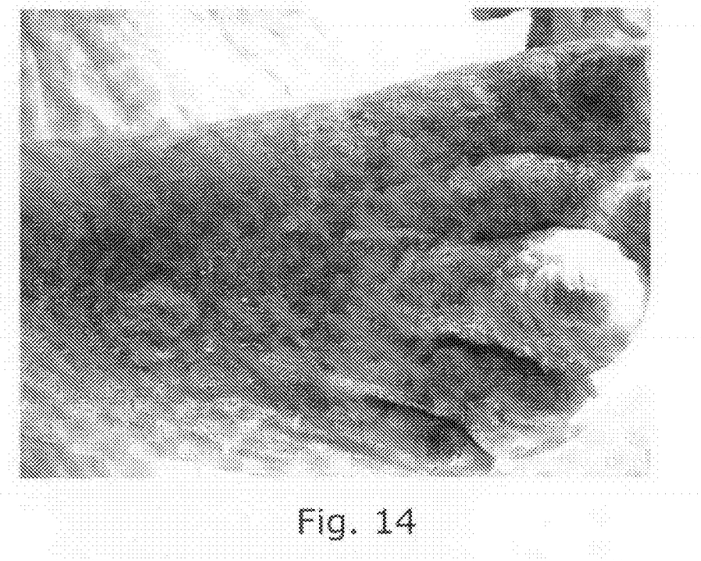
FIG. 14 shows a foot ulcer infected with *P. aeruginosa* of a 53 year old female, with a year-long history of lower leg ulceration prior to treatment.
Figure 15:
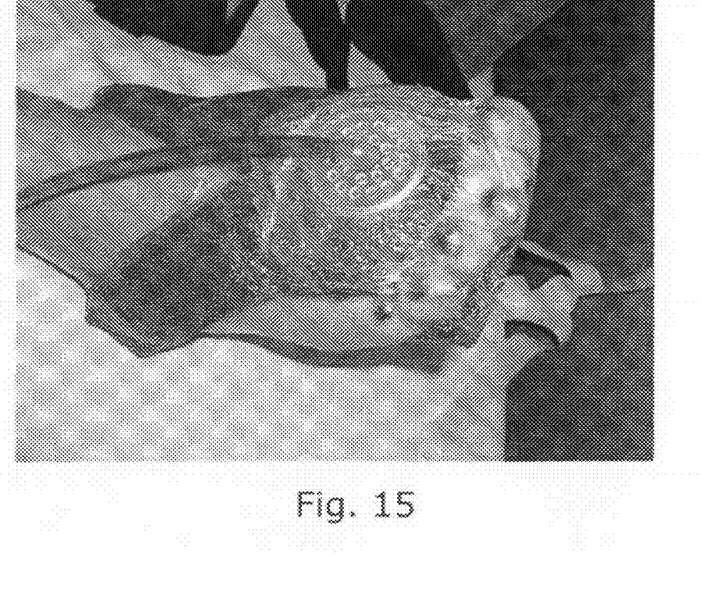
FIG. 15 shows the wound care product and the kit of the present invention as applied in combination with the delivery system of the present invention on the foot ulcer of FIG. 14.
Figure 16:
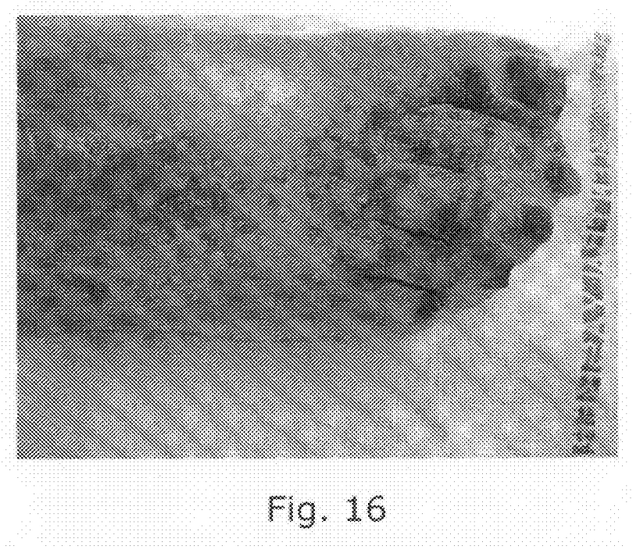
FIG. 16 shows the foot ulcer of FIGS. 14 and 15 after 6 days of treatment with the wound care product of the present invention in combination with NPWT comprising buffered acetic acid solution (day 6). The mucoid infection has been eradicated and the ulcer is now healing
Figure 17:
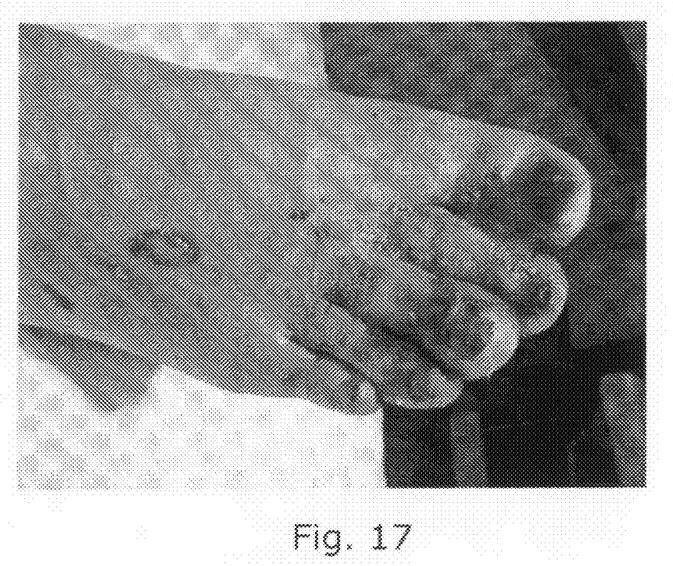
FIG. 17 shows the foot ulcer of FIGS. 14-16 at 9 days after the treatment commenced. The mucoid infection has been eradicated and the ulcer is now healing normally.

To further evaluate the clinical potential of buffered acetic acid solution towards the clinical important mucoid (alginate over-producing) P. aeruginosa phenotype, it was tested in the treatment of a chronic foot ulcer.
Medical History:
A 53 year old female, past drug-addict, with a year-long history of lower leg ulceration. The patient had been treated with compression bandages for years and numerous antibiotic courses. The presented ulcer was very painful.
Treatment:
  The treatment was performed essentially as in example 9, i.e. 6 treatments per day with buffered acetic acid followed by typically 4 h application of negative pressure between those treatments. FIGS. 14-17 shows the clinical presentation before buffered acetic acid treatment (FIG. 11), the device used for NPWT application (FIG. 12), after six days of treatment (FIG. 13), and finally nine days post treatment (FIG. 14). The ulcer has improved dramatically and improves with compression therapy even after cessation of active therapy.

REFERENCES

Novick, R. P. 1967. Properties of a cryptic high-frequency transducing phage in Staphylococcus aureus. Virology 33:155-166.
Christensen, B. B., Sternberg, C., Andersen, J. B., Palmer, R. J., Jr, Nielsen, A. T., Givskov, M. & Molin, S. (1999). molecular tools for study of biofilm physiology. Methods Enzymol 310, 20-42.
O'Toole, G. A., Pratt, L. A., Watnick, P. I., Newman, D. K., Weaver, V. B. and Kolter, R. (1999) Genetic approaches to study of biofilms. Methods Enzymol 310, 91-109.
Martineau L and Dosch H M (2007), Journal of Applied Microbiology, 103, 297-304 describes "Biofilm reduction by a new burn gel that targets nociception".
Akiyama H et al (1999); Arch Dermatol Res, 291, 570-573 describes "Effects of acetic acid on biofilms formed by Staphylococcus aureus".
WO2005/058381
WO2005/123057
WO2008/013896

The invention claimed is:

1. A method of treating a wound comprising:
   a) applying a wound care product to the wound, the wound care product comprising a liquid acidic composition comprising acetic acid in a non-dissociated form, as given by the formula $CH_3COOH$, wherein the amount of acetic acid in said liquid acidic composition is 0.5-5 wt/wt % and, wherein the liquid acidic composition has a pH below 4.76; and
   b) applying a negative pressure to the wound,
   wherein the liquid acidic composition is applied to the wound for a period of 10-40 min., the starting point of the period being when the liquid acidic composition comprising acetic acid is put in contact with the wound and the end point being when the negative pressure is applied, and
   wherein said wound is a chronic wound comprising a bacterial infection and a mature biofilm.

2. The method according to claim 1, wherein said bacterial infection comprises bacteria selected from the group consisting of *P. aeruginosa* and *S. aureus*.

3. The method according to claim 1, wherein said wound care product is applied using a spray, a gel, a dressing, a paste or a foam.

4. The method according to claim 1, wherein said wound care product is applied in combination with at least one additional antibacterial compound.

5. The method according to claim 4, wherein said additional antibacterial compound is an antibiotic, selected from the group consisting of amino glycosides, macrolides, fluoroquinolones, ceftazidimes, tetracyclines, sulfonamides, beta-lactams, oxazolidiones, and antimicrobial peptides.

6. The method according to claim 4, wherein said additional antibacterial compound is selected from the group consisting of xylitol, framycetin, fusidic acid, nitrofural, phenylmercuric nitrate, benzododecinium, triclosan, cetylpyridinium, aluminium chlorohydrate, povidone-iodine, clioquinol, benzalkonium, chlorhexidine, iodoform, and hypochloric acid.

7. The method according to claim 1, wherein the negative pressure is applied for a period in the range of 0.5-18 h.

8. The method according to claim 1, wherein the said bacterial infection comprises mucoid (alginate over-producing) *P. aeruginosa*.

* * * * *